(12) United States Patent
Eriksson et al.

(10) Patent No.: US 7,638,292 B2
(45) Date of Patent: Dec. 29, 2009

(54) IMMUNOASSAY

(75) Inventors: Susann Eriksson, Åbo (FI); Kim Pettersson, Åbo (FI)

(73) Assignee: University of Turku, Turun Yliopisto (FI)

( * ) Notice: Subject to any disclaimer, the term of this patent is extended or adjusted under 35 U.S.C. 154(b) by 0 days.

(21) Appl. No.: 11/979,977

(22) Filed: Nov. 13, 2007

(65) Prior Publication Data

US 2008/0153109 A1    Jun. 26, 2008

Related U.S. Application Data

(63) Continuation of application No. 10/819,213, filed on Apr. 7, 2004, now Pat. No. 7,348,157.

(30) Foreign Application Priority Data

Apr. 30, 2003    (FI) .................................. 20030652

(51) Int. Cl.
    *G01N 33/00* (2006.01)

(52) U.S. Cl. ...................... 435/7.94; 435/7.1; 435/7.92; 435/962; 435/967; 435/973; 436/518; 436/524; 436/528; 436/540; 436/546; 436/548; 436/172; 436/175; 530/403

(58) Field of Classification Search ............... 435/4, 435/7.1, 7.5, 962, 7.92–7.95, 288.4, 967, 435/973, 961, 971; 436/518, 524, 528, 540, 436/546, 548, 172, 175, 517, 523, 535, 538, 436/811, 819; 530/403
See application file for complete search history.

(56) References Cited

U.S. PATENT DOCUMENTS 6,114,180 A      9/2000  Doth et al. .................. 436/531
2004/0018577 A1* 1/2004  Campbell et al. .......... 435/7.93

FOREIGN PATENT DOCUMENTS

WO    WO 97/49994      12/1997
WO    WO 99/64868    * 12/1999

OTHER PUBLICATIONS

Katrukha et al., Degradation of cardiac troponin I: implication for reliable immunodetection, Clinical Chemistry 44 (12): 2433-2440 (1998).*

(Continued)

*Primary Examiner*—Gailene R Gabel
(74) *Attorney, Agent, or Firm*—James C. Lydon

(57)    ABSTRACT

A method for detection and/or quantification of cardiac troponin I (cTnI) in a sample derived from an individual's blood, the method being based on a sandwich immunoassay employing at least two capture antibodies and at least one tracer antibody, in which a first capture antibody is directed to the N-terminal part of cTnI, to the C-terminal part of cTnI or to the part of the cTnI midfragment, which is slightly affected by the interfering factor, and a second capture antibody is directed to another of these parts, and a tracer antibody is directed to the N-terminal part of cTnI, to the C-terminal part of cTnI or to TnC, which is complexed with cTnI.

13 Claims, 8 Drawing Sheets

OTHER PUBLICATIONS

Oh et al., Use of a Dual Monoclonal Sold Phase and a Polyclonal Detector to Create an Immunoassay for the Detection of Human Cardiac Troponin I, Clinical Biochemistry 33: 255-260 (Jun. 2000).*

Eric Davies et al., "Analytical Performance and Clinical Utility of a Sensitive Immunoassay for Determination of Human Cardiac Troponin I", *Clinical Biochemistry* 30:6, 479-490 (1997).

Gaelle Ferrieres et al., "Human Cardiac Troponin I: Precise Identification of Antigenic Epitopes and Prediction of Secondary Structure", *Clinical Chemistry* 44:3, 487-493 (1998).

Susann Eriksson et al., "Negative Interference in Cardiac Troponin I Immunoassays from a Frequently Occurring Serum and Plasma Component", *Clinical Chemistry* 49:7, 1095-1104 (2003).

Se-Kyung Oh et al., "Use of a Dual Monoclonal Solid Phase and a Polyclonal Detector to Create an Immunoassay for the Detection of Human Cardiac Troponin I", *Clinical Biochemistry* 33:4, 255-263 (2000).

Giuliani et al., "Determination of Cardiac Troponin I Forms in the Blood of Patients with Acute Myocardial Infarction and Patients Receiving Crystalloid or Cold Blood Cardioplegia," 45 *Clin.Chem.* 213-222 (1999).

Katrukha et al., "Troponin I is Released in Bloodstream of Patients with Acute Myocardial Infarction Not in Free Form But as Complex," 43 *Clin.Chem.* 1379-1385 (1997).

Bohner et al., "False-Negative Immunoassay Results for Cardiac Troponin I Probably Due to Circulating Troponin I Antibodies," 42 *Clin.Chem.* 2046 (1996).

Oh et al., Use of a Dual Monoclonal Sold Phase and a Polyclonal Detector to Create an Immunoassay for the Detection of Human Cardiac Troponin I, *Clinical Biochemistry* 33:255-260 (Jun. 2000).

Katrukha et al., "Degradation of Cardiac Troponin I: Implication for Reliable Immunodetection", *Clin.Chem.* 44: 2433-2440 (1998).

Cardiac markers section of BiosPacific on-line catalog, http://www.biospacific.com/cardiac.html) Cardiac Markers section—as provided in IDS.

* cited by examiner

IMMUNOASSAY

This application is a continuation of application Ser. No. 10/819,213, filed Apr. 7, 2004, now U.S. Pat. No. 7,348,157.

FIELD OF THE INVENTION

This invention relates to a novel immunoassay of cardiac troponin I (cTnI) in a sample derived from an individual's blood.

BACKGROUND OF THE INVENTION

The publications and other materials used herein to illuminate the background of the invention, and in particular, cases to provide additional details respecting the practice, are incorporated by reference.

Cardiac troponins I and T (cTnI and cTnT are sensitive and reliable markers of myocardial damage and their use has been recommended by scientific committees for the diagnosis of acute coronary syndromes (ACS)(1, 2). The complex molecular nature of cTnI complicates the measurements by immunoassays giving rise to large discrepancies in cTnI concentrations as measured with differently configured commercial and research assays (3, 4). This is conceivably a compound effect of the lack of an international standard and the divergent recognition of the numerous cTnI forms by the antibodies employed in the assays (5, 6). Since cTnI is a component of the troponin complex responsible for the regulation of muscle contraction, it interacts with other components of the complex, cTnT and troponin C (TnC) with a strong interaction with TnC in the presence of intracellular calcium (7). It has been shown that the main part (about 90%) of cTnI in the blood of patients with acute myocardial infarction (AMI) is in the form of the binary cTnI-TnC complex and only a small part is in the free form (8, 9). The antibodies used in immunoassays should ideally recognise both free and complexed cTnI in an equimolar manner (10) but more specifically the unrestricted recognition of the complex is of vital importance. Moreover, the use of antibodies against epitopes in the central part of cTnI has been generally recommended since the N- and C-terminal ends are susceptible to proteolytic degradation both in vivo and after sampling (10-12). The cTnI molecule contains two serine residues in positions 23 and 24 that can be phosphorylated in tissue, and it has been reported that around 50% of the cTnI in the blood of AMI patients is in the phosphorylated form (13). The structure and conformation changes following phosphorylation can significantly affect the binding of some antibodies to cTnI (10, 14). Furthermore, the two cysteine residues in positions 80 and 97 can form a disulfide bond allowing cTnI to be found in oxidized and reduced forms (15) again affecting the antigen recognition of different commercially available assays (6). Since the cTnI molecule has a high positive charge (pI 9.87) it will attract negatively charged molecules such as heparin, which in turn can interfere with the antibody-antigen interaction (10). Heparinised plasma samples are widely used in clinical laboratories and thus discrepant results compared to serum will occur if the antibodies are affected by heparin (16). Also EDTA used as anticoagulant can cause discrepancy, especially in assays utilising antibodies with different recognition of free and complexed cTnI (17), since EDTA will partly unfold the calcium-dependent troponin complex. All of the characteristics of cTnI mentioned above should be thoroughly considered in the design and development of cTnI immunoassays.

Analytical interference due to a number of more non-specific causes is a common problem that affects almost all immunoassays to some extent, resulting in false-positive or false-negative results (18). The most frequently described interfering mechanisms are those caused by heterophilic antibodies, human-anti-mouse antibodies, rheumatoid factors and complement [reviewed in (19, 20)]. Introduction of blocking agents (e.g. mouse serum or IgG) is often useful in eliminating this type of interference (21, 22). Especially false-positive results for cTnI have been frequently reported, while the number of false-negative results reported is much lower. The false-positive results have been claimed to be due to the presence of heterophilic antibodies (23), rheumatoid factor (24, 25) or an unknown macromolecular complex (26). Unrepeatable false increases have also been attributable to the presence of fibrin after incomplete separation of serum (27). More exceptionally they may result from fluid therapy given to patients (28). One report of a false-negative cTnI result was attributed to circulating cTnI autoantibodies (29) and also bilirubin and hemoglobin have been reported to give negative interference in certain cTnI assays (30).

OBJECT AND SUMMARY OF THE INVENTION

Remarkably little attention has been paid to reporting the analytical recovery of cTnI when evaluating new cTnI immunoassays, despite the well-recognised problems associated with these assays.

The object of the present invention is to provide an improved immunoassay for the determination of cTnI, where an interfering factor (IF) causing falsely low or even negative results is circumvented. The aim is to provide an assay, which accurately detects cTnI in the early phase in blood samples from patients with myocardial infarction.

This aim is achieved by the present invention, which relates to a method for detection and/or quantification of cardiac troponin I in a sample derived from an individual's blood, said method being based on a sandwich immunoassay employing at least two capture antibodies and at least one tracer antibody. According to the invention

- a first capture antibody is directed to the N-terminal part of cTnI, to the C-terminal part of cTnI or to the part of the cTnI midfragment, which is slightly affected by the interfering factor, and a second capture antibody is directed to another of the aforementioned parts, and
- a tracer antibody is directed to the N-terminal part of cTnI, to the C-terminal part of cTnI or to TnC, which is complexed with cTnI.

DETAILED DESCRIPTION OF THE INVENTION

The main part of cardiac troponin I, which is a 209 aa protein, exists as complexed with troponin C. According to one alternative, all the antibodies are directed to epitopes on the cTnI part of the complex. According to another, preferable alternative, the complex containing both cardiac troponin I and troponin C could be considered as the antigen to be determined. In this case the antibodies could be directed both to epitopes on troponin C and on cardiac troponin I.

The 209 aa cardiac troponin I protein comprises an "N-terminal part" comprising the amino acids 1-29, a stable part, "midfragment" comprising the amino acids 30-109, and a "C-terminal part" comprising the amino acids 110-209.

Figure 1:
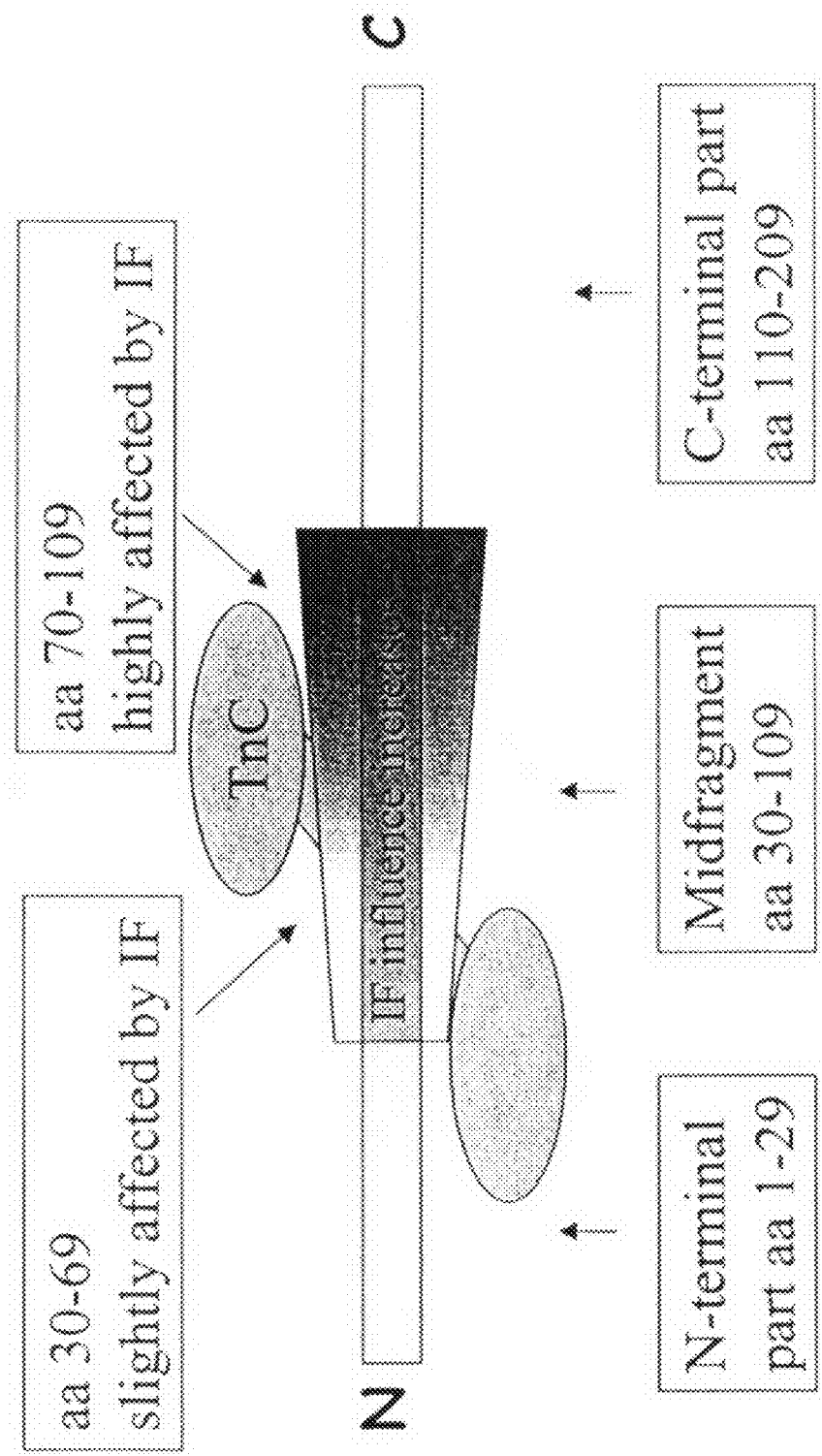
FIG. 1 shows the cTnI protein, its N-terminal part, its C-terminal part, and its midfragment, which in turn can be divided in two parts: a highly IF-affected part and a slightly IF-affected part (IF=interfering factor).

The midfragment is stable and most of the known cTnI assays employ antibodies directed to epitopes in this region. The inventors of the present invention have, however, found that the midfragment is affected by an interfering factor (IF), and this factor is found to disturb the activity of the antibody directed to this region. The strength of the interfering factor increases from aa 30 to aa 109. The region 70-109 aa is here defined as the part of the cTnI midfragment which is highly influenced by the interfering factor. The remaining part, namely 30-69 aa is here defined as the part of the cTnI midfragment which is slightly affected by the interfering factor. See FIG. 1.

The N-terminal part is susceptible to cleavage, giving rise to a 1-29 aa fragment. The C-terminal part is more stable then the N-terminal part, but can be cleaved in a region between 148 and 190 aa. The remaining part of the C-terminal is more stable, but cleaving can occur in the region 110-137 aa.

When suitable antigen epitopes are selected, the highly IF affected part of the cTnI midfragment should be avoided.

According to this invention, a first capture antibody is directed to the N-terminal part of cTnI, to the C-terminal part of cTnI or to the part of the cTnI midfragment, which is slightly affected by the interfering factor, and a second capture antibody is directed to another of the aforementioned parts, and a tracer antibody is directed to the N-terminal part of cTnI, to the C-terminal part of cTnI or to TnC, which is complexed with cTnI.

The wording stating that the antibody is directed to a certain part of the cTnI protein shall be interpreted so that more than 50% of the amino acids, preferably more than 60%, especially 100%, constituting the epitope to which the antibody binds are located within said part of the cTnI protein.

Preferably, a first capture antibody is directed to the part of the cTnI midfragment, which is slightly affected by the interfering factor and a second capture antibody is directed to the N-terminal or to the C-terminal part of cTnI, and a tracer antibody is directed to the C-terminal part of cTnI. For example, the first capture antibody is directed to the epitope region 30-69 aa, preferably 41-49aa, the second capture antibody is directed to the epitope region 148-209 aa, preferably 190-196 aa, and the tracer antibody is directed to the epitope 110-148 aa, preferably 137-148.

According to another preferable embodiment, three capture antibodies are used.

According to a particularly preferable embodiment, the first capture antibody is directed to the part of the cTnI midfragment, which is slightly affected by the interfering factor and a second capture antibody is directed to the C-terminal part of cTnI, and a third capture antibody is directed to the N-terminal part of cTnI, and the tracer antibody is directed to TnC. For example, the first capture antibody is directed to the epitope region 30-69 aa, preferably 41-49 aa, the second capture antibody is directed to the epitope region 148-209 aa, preferably 190-196 aa, and the third capture antibody is directed to the epitope region 1-29 aa, preferably 23-29 aa.

The assay can be carried out as a heterogeneous assay, where the capture antibody is biotinylated in order to be able to bind to a streptavidin coated solid phase. The captured antibody together with the bound cTnI can be separated from the incubation mixture before it is subjected to the tracer antibody in a separate step. The tracer antibody can be labelled with any detectable label, preferably a luminescent label. Alternatively, the tracer antibody can be added simultaneously, e.g. according to the all-in-one dry chemistry concept (reference 34). After incubation a washing step follows. According to a third alternative, the heterogeneous assay can be carried out in immunochromatographic format according to well known technology.

Alternatively, the assay can be carried out as a homogeneous assay, where no separation is necessary before the addition of the tracer antibody, which can be added simultaneously with the capture antibody. In this alternative, the capture antibody is preferably attached to a dye in the form of a small particle, especially a nanoparticle, or to a luminescent molecule. An especially preferable homogeneous assay is a homogeneous energy transfer assay, where the capture antibody is attached to a luminescent lanthanide chelate, which is excited by radiation and capable of transferring energy to the label of the tracer antibody. Such assays are described in the art, for example in WO 98/15830 and EP 965043.

By using suitable dyes the homogeneous assay can be carried out in a serum, a plasma sample or a whole blood sample.

Alternatively, the assay can be carried out using a homogeneous detection system ("Fluorescence Energy Transfer Dye System") but in combination with a built-in wash system based on capillary forces such as used in the Triage® Cardiac System (Biosite Diagnostics).

The invention will be illuminated by the following non-restrictive Experimental Section.

EXPERIMENTAL SECTION

We have studied the analytical recovery of tissue derived cTnI (ternary troponin complex) in different sample matrices obtained from healthy individuals or patients with symptoms of chest pain using antibodies recognising different cTnI epitopes. The cTnI concentration in admission and monitoring samples from myocardial infarction (MI) patients was also measured with two investigative and two commercial cTnI assays. The results show the frequent occurrence of an as yet unidentified serum and plasma component that can severely interfere with the binding of antibodies especially to epitopes of the stable midfragment of cTnI.

Materials and Methods

Reagents

Human cardiac troponin complex (native, tissue derived complex of cTnI-cTnT-TnC) and monoclonal antibodies (Mabs) specific for cTnI were obtained from HyTest Ltd. Five Mabs were used, of which three have epitopes in the stable part of cTnI (Mab 1 epitope in the region of amino acid residues 35-55, Mab 2 and Mab 5 epitopes in the region of amino acid residues 80-95), one has a N-terminal epitope in the region of 20-35 (Mab 3) and one have a C-terminal epitope in the region of 185-200 (Mab 4). All antibodies recognise both free cTnI and cTnI in complex with TnC or TnT or both. Standards were prepared by diluting the cardiac troponin complex in a buffer containing 7.5% bovine serum albumin, 50 mmol/L Tris-HCl pH 7.75, 15 mmol/L NaCl and 0.5 g/L NaN$_3$. The cTnI concentration of the troponin complex stock reported by the manufacturer was used to assign the cTnI concentrations of the standard dilutions. The standards were stored at −20° C. until use, and a new set of standards was taken for every assay.

Samples

Ten plasma samples with EDTA as anticoagulant and matched serum samples were taken from apparently healthy volunteers at the Department of Biotechnology, University of Turku. Heparin plasma samples from 16 chest pain patients were taken at admission and for monitoring up to 97 h at the Department of Internal Medicine, Oulu University Hospital. The corresponding serum samples were initially analysed at the Laboratory of Oulu University Hospital with AxSYM troponin I (Abbott Laboratories) and ACS:180 cTnI (Bayer Diagnostics) (31). All samples were stored at −20° C. or at −70° C. for long-term storage.

Labelling of Antibodies with Lanthanide Chelate or Biotin

The intrinsically fluorescent europium chelate used for labelling of the detection antibodies was kindly provided by M. Sc. Jaana Rosenberg (Department of Bio-Organic Chemistry, University of Turku, Finland). The chelate was a europium (III) chelate of 2,2', 2",2'''-[[4-[(4-isothiocyanatophenyl)ethynyl]pyridine-2,6-diyl]bis(methylenenitrilo)]tetrakis(acetic acid) (32). The labelling of antibodies was performed in 50 mmol/L sodium carbonate buffer, pH 9.8, with a 100-fold molar excess of chelate at room temperature over night (16-20 h). The labelled antibody was separated from excess free label on a Superdex 200 HR 10/30 gel filtration column equilibrated and run with 50 mmol/L Tris-HCl pH 7.75, 15 mmol/L NaCl, 0.5 g/L NaN$_3$ at 25 mL/h and 0.5-mL fractions were collected. The fractions containing labelled protein were pooled, the protein concentration was determined with the Bio-Rad Protein Assay (Bio-Rad) and the degree of labelling was determined using a europium calibration solution. Bovine serum albumin was added to a final concentration of 1 g/L and the solution was filtered through a 0.22 μm pore size filter and stored at +4° C. The labelling degrees of the antibodies were 6-12 Eu-chelates per molecule of IgG.

Biotin-isothiocyanate (J. Rosenberg) was used for the biotinylation of antibodies. The antibody was biotinylated with a 30-fold molar excess of biotin-isothiocyanate in 50 mmol/L sodium carbonate buffer, pH 9.8, at room temperature for 4 h. The biotinylated antibody was separated from free biotinylation reagent by passing the reaction twice through disposable NAP-5 or NAP-10 columns (Amersham Biosciences AB) with 50 mmol/L Tris-HCl pH 7.75, mmol/L NaCl, 0.5 g/L NaN$_3$ as eluent. Bovine serum albumin was added to a final concentration of 1 g/L and the solution was filtered through a 0.22 μm pore size filter and stored at +4° C.

Immunoassays

The biotinylated capture antibody Mab 1, 400 ng in 25 μl of DELFIA® Assay Buffer (Perkin Elmer Life Sciences, Wallac Oy) per well, was attached to streptavidin-coated microtiter wells (Innotrac Diagnostics Oy) for 1 h at 35° C. without shaking. Unbound capture antibody was removed by washing the wells, and 100 ng of Eu-labelled antibody (Mab 2, 3, 4 or 5) was added in a volume of 20 μl followed by 20 μl of standard or sample. The wells were incubated for 1 h at 36° C. with slow shaking and the wells were washed and dried for 5 min under a stream of hot dry air. The time-resolved europium fluorescence was measured directly from the dry surface in a Victor™ 1420 Multilabel Counter (Perkin-Elmer Life Sciences, Wallac Oy). The assay with four antibodies using Mabs 1 and 3 as capture antibodies and Mabs 2 and 4 as detection antibodies (Mabs 1 and 3/Mabs 2 and 4) was performed in the same way except that 200 ng of each biotinylated capture antibody was used. The lower detection limits (+2SD of blank) were approximately 0.031 g/L and 0.02 μg/L for the Mab 1/Mab 2 assay and the Mabs 1 and 3/Mabs 2 and 4 assay, respectively.

Analytical Recovery

Unless otherwise stated, the analytical recovery of standard cTnI was measured after adding ternary troponin complex corresponding to 30 μg/L of cTnI (final concentration) to the samples. The signal from the spiked sample was compared to the signal of a buffer (7.5% bovine serum albumin, 50 mmol/L Tris-HCl pH 7.75, 15 mmol/L NaCl and 0.5 g/L NaN$_3$) spiked in the same way and the recovery was calculated based on the assumption that the recovery in buffer was 100%. The recovery of endogenous cTnI was tested after adding a small volume of a patient sample with high cTnI concentration to the samples. The cTnI concentration in the patient sample was determined with the Mab 1/Mab 2 assay against standards prepared from the ternary troponin complex stock solution.

Statistical Analysis

Statistical analysis was performed using Microcal™ Origin® version 6.0.

Results

Analytical Recovery of cTnI in Serum and EDTA Plasma

The analytical recovery of standard cTnI, added as ternary troponin complex corresponding to a final cTnI concentration of 30 μg/L or 500 μg/L, and cTnI from a serum sample with high cTnI concentration, added to a final concentration of 9 μg/L, was measured in serum and EDTA plasma from healthy volunteers with the original Mab 1/Mab 2 assay. The recovery of cTnI in individual serum and EDTA plasma samples is shown in Table 1. The mean recovery in serum samples spiked to 30 μg/L was 43.8% (range 7.0-71.2%), and 27.1% (range 5.5-38.6%) in EDTA plasma samples. When samples were spiked to 500 μg/L, the mean recovery was 81.3% (range 66.1-88.8%) and 74.0% (range 61.6-80.9%) in serum and EDTA plasma samples, respectively. When samples were spiked with endogenous cTnI to a final concentration of 9 μg/L, the mean recovery was 48.1% (range 22.4-66.2%) in serum and 38.5% (range 23.6-51.0%) in EDTA plasma.

recovery sample (data not shown), different combinations with Mabs 1, 2, 3 and 4 were tested. Since it is known that the N- and C-terminal parts of the cTnI molecule, to which Mabs 3 and 4 bind, may be rapidly degraded, it was decided to retain Mabs 1 and 2 so that detection of cTnI would be possible in samples containing degraded cTnI. The four combinations tested were Mabs 1+3 (capture) with Mabs 2+4 (tracer), Mabs 1+4 (capture) with Mabs 2+3 (tracer), Mabs 2+3 (capture) with Mabs 1+4 (tracer), and Mabs 2+4 (capture) with Mabs 1+3 (tracer). The final combination was selected based on a compromise between high specific signals, background signal levels in samples from healthy individuals and increased recovery of standard cTnI in samples showing low recovery

TABLE 1

Recovery (%) of cTnI as part of the ternary troponin complex added to a final cTnI concentration of 30 or 500 μg/L and recovery (%) of cTnI from a serum sample of an AMI patient added to a final concentration of 9 μg/L to serum or EDTA plasma from 10 healthy volunteers. The recoveries in samples 3 and 10 were significantly different from the mean recovery in serum spiked to 30 μg/L ($p = 0.0014$ and $p = 0.0003$), in plasma spiked to 30 μg/L ($p = 0.0013$ and $p = 0.0002$), in serum spiked with endogenous cTnI ($p = 0.0018$ and $p = 0.0003$) and in plasma spiked with endogenous cTnI ($p = 0.0206$ and $p = 0.0001$). The recovery in sample 10 was significantly different from the mean also in serum and plasma spiked to 500 μg/L ($p < 0.0001$ and $p = 0.0002$), while the recovery in sample 3 was not ($p = 0.7626$ and $p = 0.2166$).

| Sample | cTnI 30 μg/L | | cTnI 500 μg/L | | Endogenous cTnI 9 μg/L | |
|---|---|---|---|---|---|---|
| | Serum | Plasma | Serum | Plasma | Serum | Plasma |
| 1 | 65.9 | 33.6 | 87.6 | 71.7 | 56.5 | 51.0 |
| 2 | 53.3 | 31.3 | 86.1 | 79.1 | 53.7 | 39.2 |
| 3 | 14.4 | 10.7 | 81.9 | 76.7 | 28.7 | 32.0 |
| 4 | 71.2 | 38.6 | 88.8 | 78.6 | 50.8 | 38.8 |
| 5 | 33.9 | 19.3 | 81.5 | 66.4 | 38.0 | 35.2 |
| 6 | 47.4 | 33.6 | 82.0 | 79.4 | 51.0 | 40.9 |
| 7 | 45.2 | 31.0 | 84.1 | 80.9 | 51.8 | 38.2 |
| 8 | 55.0 | 35.6 | 77.2 | 75.7 | 66.2 | 43.9 |
| 9 | 44.7 | 31.6 | 77.2 | 70.1 | 61.6 | 41.8 |
| 10 | 7.0 | 5.5 | 66.1 | 61.6 | 22.4 | 23.6 |
| Mean ± SD (%) | 43.8 ± 20.5 | 27.1 ± 11.2 | 81.2 ± 6.6 | 74.0 ± 6.4 | 48.1 ± 14.1 | 38.5 ± 7.3 |

Recovery with different antibody combinations

Figure 2:
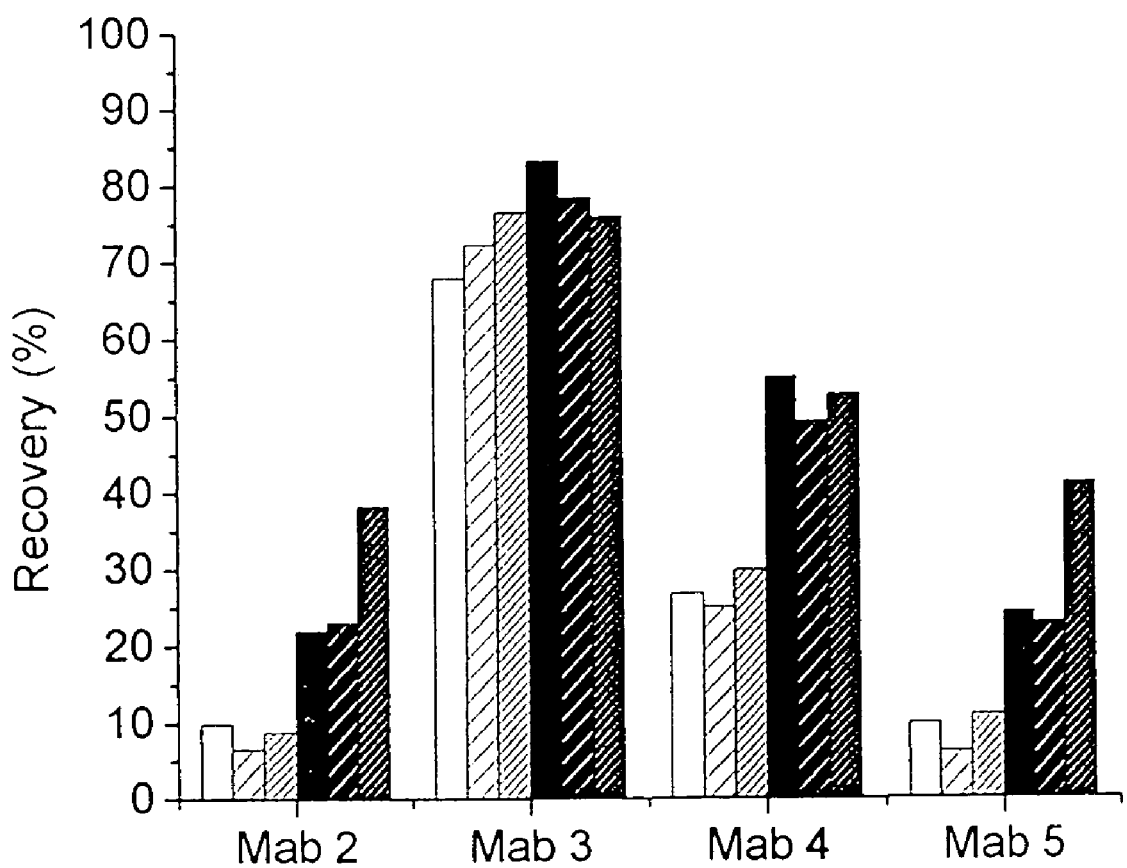
FIG. 2 shows the analytical recovery of standard cTnI using different tracer antibodies together with Mab 1 as capture antibody. The white or light shaded bars represent EDTA plasma sample 10 (low recovery) and the black or dark shaded bars represent EDTA plasma sample 8 ("normal" recovery). The bars with no shading represent samples spiked to 0.3 µg/L cTnI, the bars with sparse diagonal lines samples spiked to 3.0 µg/L cTnI and the bars with dense diagonal lines samples spiked to 30.0 µg/L. Mab 2 and 5 have the same epitope in the central part of the cTnI molecule, Mab 3 has an N-terminal epitope and Mab 4 has a C-terminal epitope.

Different antibodies (Mabs 2, 3, 4 and 5) were tested as detection antibodies with Mab 1 as capture antibody in order to see if the recovery of cTnI was dependent on which antibodies were used. EDTA plasma samples 8 ("normal" recovery) and 10 (low recovery) were spiked with cTnI to final concentrations of 0.3, 3 and 30 μg/L. The recovery was approximately 10% in sample 10 and 20-40% in sample 8, with both Mab 2 and Mab 5, which share the same epitope in the central part of cTnI. Using Mab 3, which has an epitope in the N-terminal region of cTnI, for detection gave significantly improved recovery and the difference in recovery between sample 8 and 10 was considerably decreased. Mab 4, with a C-terminal epitope also gave improved recovery compared to Mabs 2 and 5, but with sample 10 the recovery still remained below 30%. The recovery with the different antibodies is shown in FIG. 2.

Development of cTnI Assay Using Two Capture and Two Detection Mabs

The recovery results with different antibodies provided the basis for development of a new cTnI assay format with two capture Mabs and two detection Mabs. Based on the finding that recovery with Mab 3 as the capture and Mab 4 as the detection antibody was close to 100% even with the low with the Mab1/Mab 2 combination. The final assay format with two capture and two tracer antibodies was Mabs 1+3/Mabs 2+4.

Analysis of Admission and Follow-Up Samples from Chest Pain Patients

Figure 3:
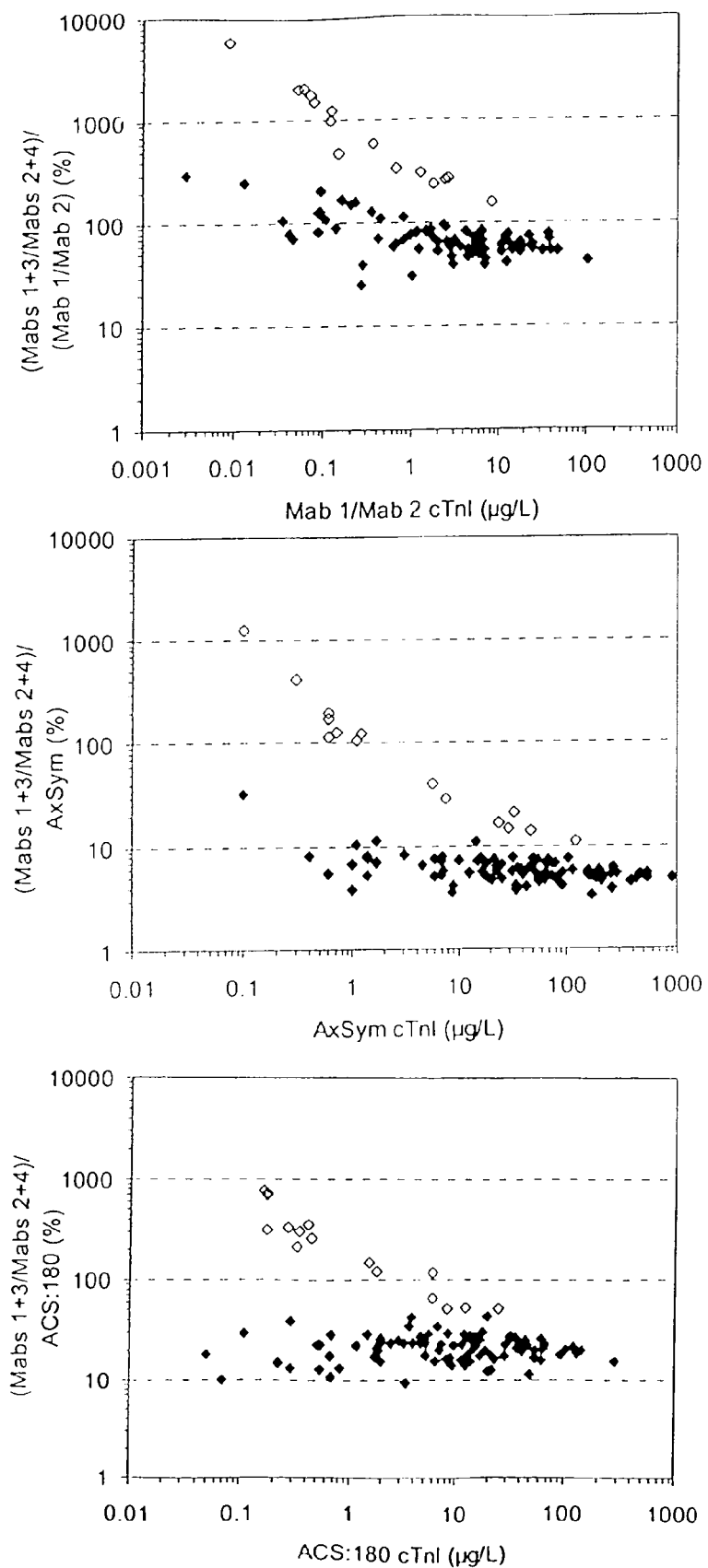
FIG. 3 shows samples from 16 AMI patients measured with two research cTnI assays (Mab 1/Mab 2 and Mabs 1+3/Mabs 2+4 assays) and two commercial cTnI assays (AxSym and ACS:180). The cTnI concentration is plotted against the percentage that the Mabs 1+3/Mabs 2+4 assay gives of cTnI result with the corresponding assay. Samples from patients 1 and 5 (open squares), samples from the other 14 AMI patients (filled squares).
Figure 4A:
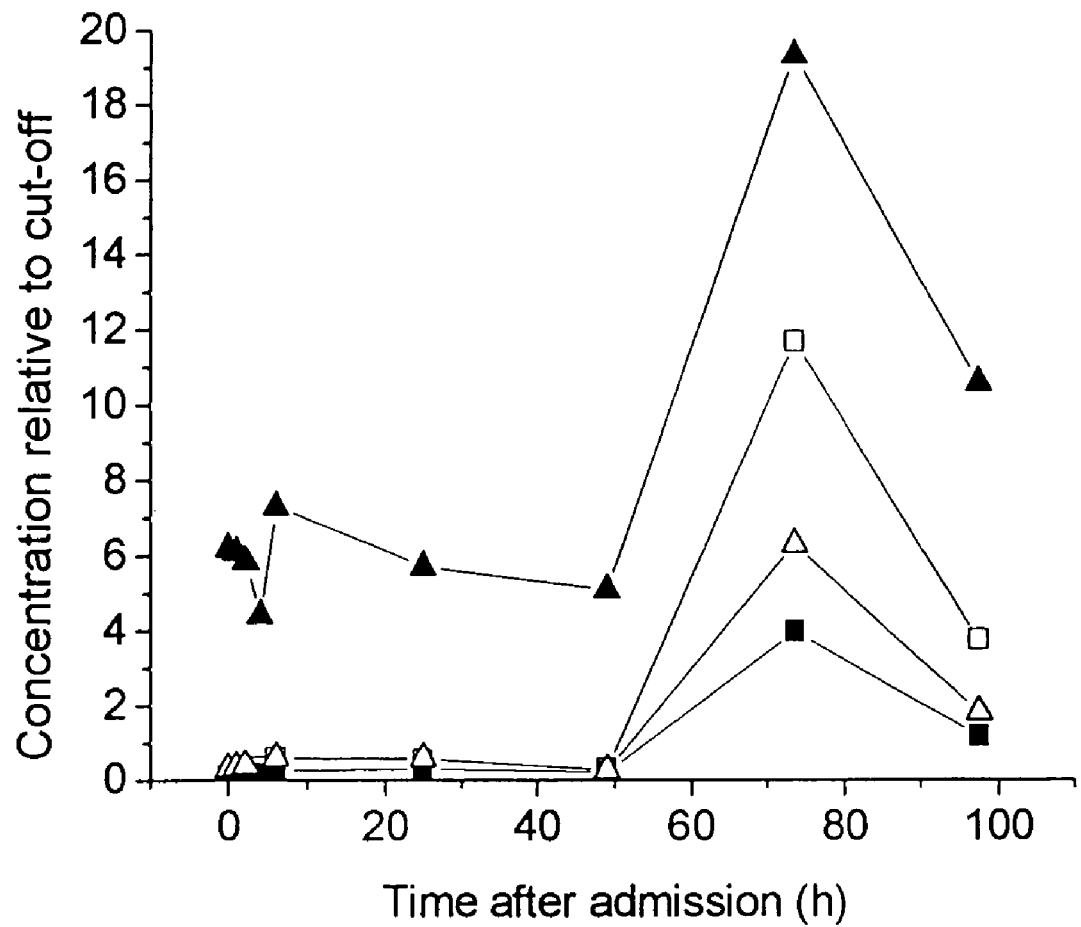
FIG. 4 shows individual cTnI release profiles for patients 1 (A) and 5 (B) relative to the cut-off of the respective cTnI assay. The samples were measured with four immunoassays: Mab 1/Mab 2 (Δ), Mabs 1+3/Mabs 2+4 (▲), AxSym (□) or ACS:180 (■). The inset in (B) shows the release profile in full scale.
Figure 4B:
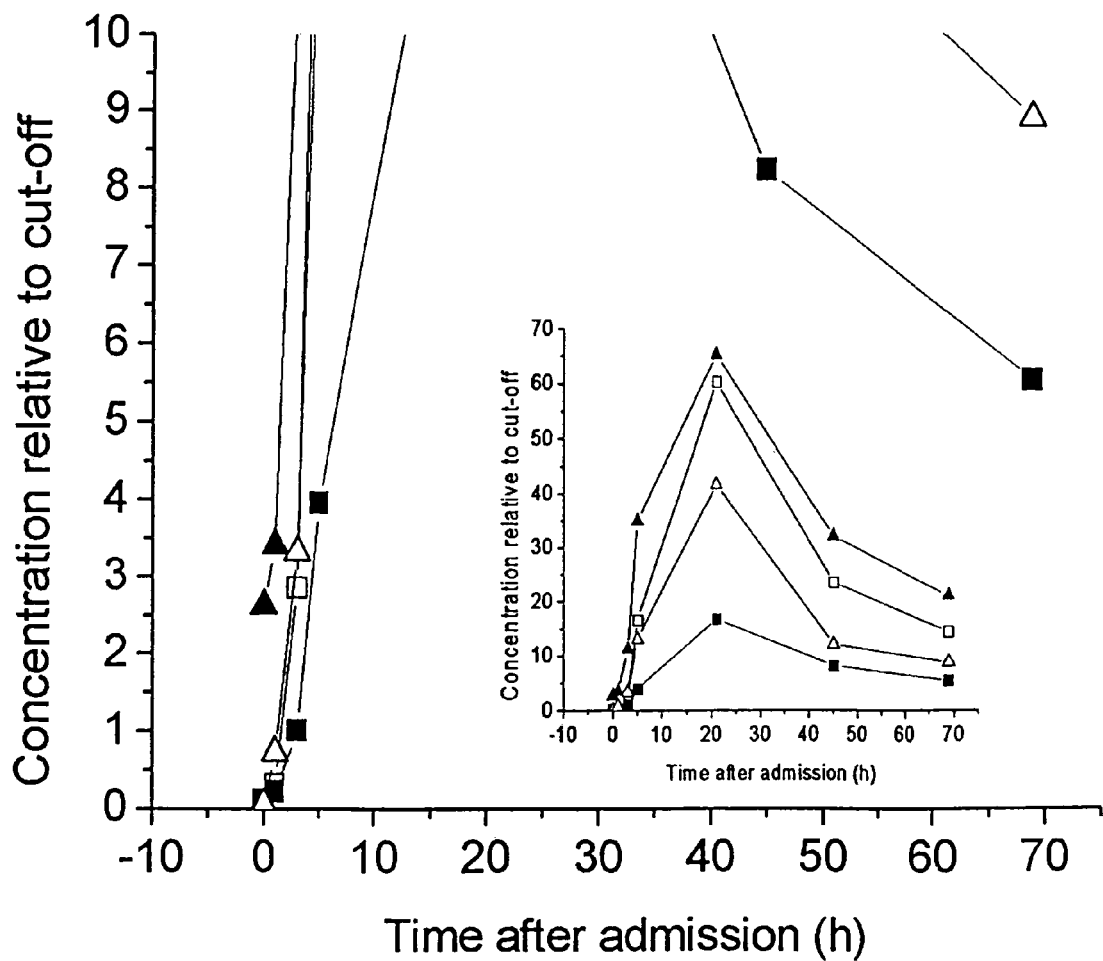
Figure 6:
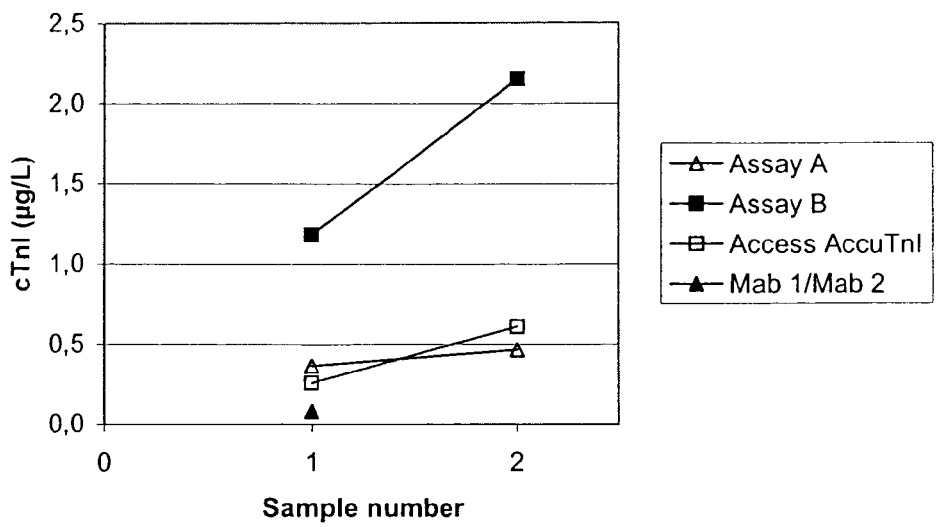
FIG. 6 shows cTnI release profiles for two patients (a and b) in samples taken at admission (1) and 6 hours later (2), measured with assays according to this invention, Assay A and B, and previously known assays.
Figure 6:
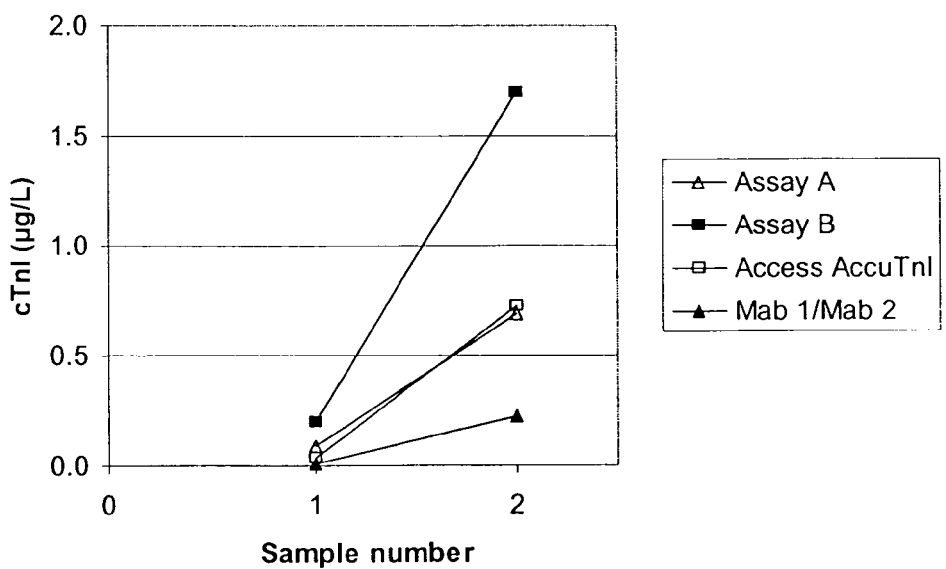

The cTnI results from 16 patients presenting with chest pain (admission sample plus 3-8 follow-up samples, totally 108 samples) with the previously known Mab 1/Mab 2 assay and the new Mabs 1+3/Mabs 2+4 assay were compared with each other and with the serum sample results from the commercially available AxSym and ACS:180 cTnI assays. Two patients (patients 1 and 5) showed clearly higher relative results with the Mabs 1+3/Mabs 2+4 assay than with any of the other assays, while the results from all assays were in good agreement for the other patients (FIG. 6). As can be seen in FIG. 3, the differences between the four assays were considerable, due to differences in calibration and in antibody specificity. Our investigational Mab 1/Mab 2 and Mabs 1+3/Mabs 2+4 assays that use the same calibration standards gave quite similar results, with slightly lower concentrations with the Mabs 1+3/Mabs 2+4 assay. The Mabs 1+3/Mabs 2+4 assay gave much lower results, generally less than 10% of the concentration with AxSym, and about 20% of that obtained with ACS:180. The manufacturers' recommended clinical MI cut-off for AxSym cTnI was 2.0 µg/L and for ACS:180 cTnI it was 1.5 µg/L at the time when the analyses were performed. The clinical cut-offs for our investigational assays have not been finally established, but an estimation based on correlation with the two commercial assays would suggest a cut-off around 0.2 µg/L for both assays (e.g. AxSyM with a cut-off of 2.0 µg/L gives approximately 10 times higher cTnI concentrations than our assays). When the data was normalized using these cut-off values for patients 1 and 5 (FIGS. 4A and 4B), it was evident that especially for patient 1, the new Mabs 1+3/Mabs 2+4 assay would suggest an MI diagnosis earlier than any of the other assays. Also for patient 5, the Mabs 1+3/Mabs 2+4 assay gives concentrations above the cut-off starting from the first sample. The difference between the assays was largest in the first samples with smaller cTnI concentrations, and the relative differences decreased in samples taken later in the monitoring of the patients. Based on the electrocardiograms, patient 1 was diagnosed with unstable angina with ST-segment depression and patient 5 was classified as having a ST-segment elevation infarction.

CONCLUSIONS

This study is the first report of a frequently occurring serum and plasma component that seriously interferes with the determination of circulating cTnI. While at this point we have not been able to identify this component, some essential characteristics have been clarified regarding its occurrence and interference with cTnI measurements. More importantly, based on these observations an alternative way of selecting antibodies for cTnI assays can be recommended, whereby the inhibiting effect of the interfering factor can be avoided or at least alleviated. This finding will be of central importance for the development of new cTnI assays with improved and standardised performance.

Based on our recovery tests with different antibodies we conclude that the antibodies against mid-fragment epitopes are most affected by the interfering factor, especially Mabs 2 and 5 with epitopes around amino acids 80-95. Mab 1 of the mid-fragment (epitope around amino acids 35-55) is clearly less affected but it was difficult to fully estimate the influence of the interfering factor on individual antibodies since the tests were always performed with a combination of two antibodies. The N-terminal and C-terminal epitopes were affected to a much lesser extent and especially the N-terminal epitope seemed almost unaffected. Our results indicate that cTnI assays that use antibodies against epitopes situated in the central, stable part of cTnI give falsely too low cTnI concentrations in samples containing the interfering factor, and since the recommendation to use such antibodies is generally accepted, it is likely that most commercially available cTnI assays will be affected by this unknown component. Both of the commercial cTnI assays used for measuring the patient samples employ antibodies against the stable part of the molecule (33) and, based on the cTnI results from patients 1 and 5, both are seriously affected by the interfering component. According to Collinson et al. the epitopes of the antibodies used in the ACS: 180 assay are in the region of amino acids 30-40 and 70-88, while for antibodies employed in the AxSym assay the epitopes comprise amino acids 20-39 and 87-91 (33).

We suggest that the mechanism of action of the interfering factor is due to blocking of certain mid-fragment epitopes on cTnI presumably by non-covalent binding to the central part of cTnI. The effect was somewhat more prominent with tissue derived ternary troponin complex (standard material) than with endogenous cTnI forms and more evident in EDTA plasma than in serum. Based on our recovery experiments we know that the interfering factor binds very rapidly to cTnI causing low recovery even if cTnI is added immediately prior to the assay indicating that it has a high affinity towards cTnI. The interfering factor appeared to be present in small and limited amounts, since spiking of samples with more cTnI resulted in significantly higher recovery apparently by saturating the interfering factor. Moreover, in the samples from patients 1 and 5 the increasing effect provided by the assay with four antibodies was greatest in the first samples when only little cTnI was released. As more cTnI was subsequently released, the inhibiting effect of the interfering factor was gradually diminished.

Based on our results, the consequences of the interfering factor on cTnI measurements should be taken into careful consideration. It will cause variable inhibition of the cTnI immunoreactivity, from mild to very severe inhibition depending on the amount of interfering factor in the sample. The preliminary results obtained with patients 1 and 5 showed that the interfering factor had the greatest effect on cTnI measurements when there was only little cTnI present in the sample, such as in the early hours of an MI or unstable angina event. Samples taken early after a cardiac event might give a negative result since all of the released cTnI will be masked by the interfering factor. Later in the progression, when more cTnI is released, more cTnI will be measured since the interfering factor is present in only a limited amount and will be saturated by the released cTnI. This means that in patients with high concentrations of the interfering factor, the MI or unstable angina event might be totally overlooked, especially if a patient is discharged after the first negative cTnI measurements.

Our solution to the described interference problem is a multi-antibody assay approach to ensure detection of cTnI in the presence of the interfering factor. Since the most "interference free" antibodies are against epitopes in the terminal parts of the molecule, which are not present in fragmented cTnI molecules, combinations with mid-fragment antibodies provide a viable option, which allows altogether four possibilities for sandwich formation.

In order to further evaluate this theory, we tested two additional assays according to this principle, namely Assay A and Assay B and compared the results with previously known assays.

Assay A uses two biotinylated monoclonal antibodies for capture of cTnI to the solid phase of streptavidin coated single microtiter wells. One capture antibody is directed to aa 41-49 and the other to aa 190-196. The detection antibody, which is labelled with a stable inherently fluorescent europium chelate, is directed to aa 137-148 of cTnI. The assay is based on the all-in-one dry chemistry concept (reference 34). Briefly, all components are built into the well in a dry stable form. The Innotrac Aio Immunoanalyzer is used for performing the assay. Addition of 20 µl of sample (serum, plasma or whole blood) and 10 µl of assay solution starts the reaction. After 15 minutes of incubation the well is washed six times with assay solution and briefly dried. The signal from the detection antibody is measured using time-resolved fluorometry. The assay is performed in duplicate wells and reported result is the mean reading from two wells.

Assay B uses three biotinylated monoclonal antibodies for capture of cTnI; one directed to aa 23-29, one to aa 41-49 and one to aa 190-196. The detection antibody is directed to TnC, i.e. the assay measures the cTnI-TnC complex. The result is reported as the amount (ng/mL) of cTnI in order to facilitate comparison between assays. Assay B is also based on the all-in-one dry chemistry concept and performed in the same way as Assay A.

Assay Immunol is a commercial cTnI assay manufactured by Bayer Diagnostics.

Assay Access AccuTnI is a commercial cTnI assay manufactured by Beckman Coulter.

Figure 5:
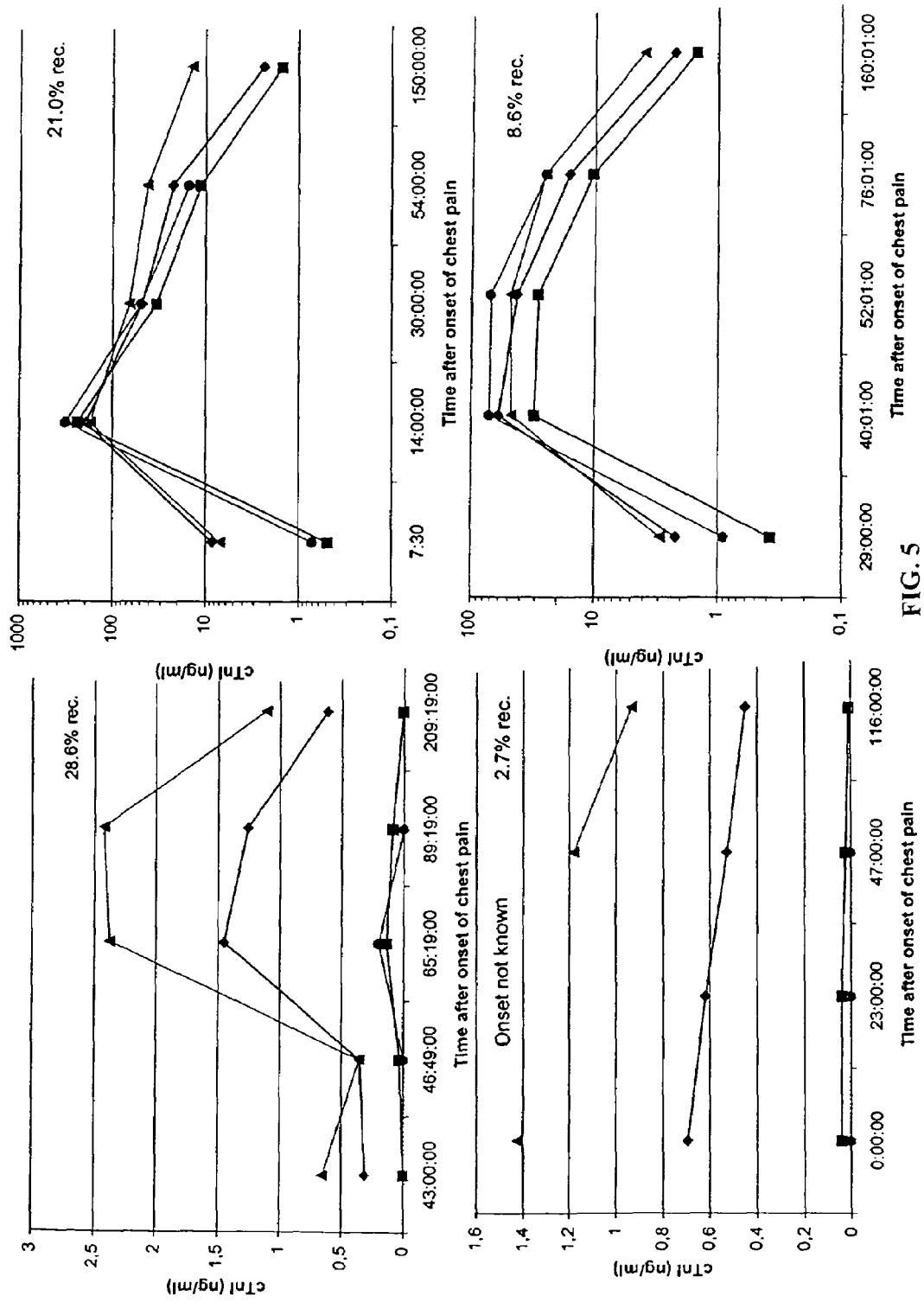
FIG. 5 shows individual cTnI release profiles for four patients presenting with chest pain measured with assays according to this invention, Assay A (diamond) and Assay B (triangle), which are both designed to be minimally affected by IF, and previously known assays, namely Assay Mab 1/Mab 2 (square), which is seriously affected by IF, and a commercial cTnI assay, Immunol (circle). The time after onset of chest pain is shown on the x-axis. For one patient the onset was not known. The cTnI concentrations in B and D are shown in logarithmic scale. The analytical recovery of added standard cTnI in the admission sample as measured with the Mab 1/Mab 2 assay is indicated in the top right corner.

In FIG. 5, the Mab 1/Mab 2 assay, which uses a monoclonal cTnI antibody directed to aa 41-49 for capture and a monoclonal cTnI monoclonal cTnI antibody directed to aa 87-91 for detection, was performed as an all-in-one assay (same assay protocol as for Assay A and B), and not as described in the Materials and Methods section. It can be seen that the new assays Assay A and Assay B in all patients give clearly higher cTnI results at onset than the previously known assays, which give false negative results at this point.

FIG. 6 shows cTnI release profiles for two patients presenting with chest pain. CTnI was measured with assays according to this invention, Assay A and B, and previously known assays, namely a commercial assay, Access AccuTnI and Assay Mab 1/Mab 2. Sample 1 was taken at admission to emergency care and sample 2 was taken 6 hours later. The analytical recovery of 3 µg/L cTnI was 34.2% in sample 1 from patient a, and 13.1% in sample 1 from patient b when measured with Assay Mab 1/Mab 2.

Figure 7:
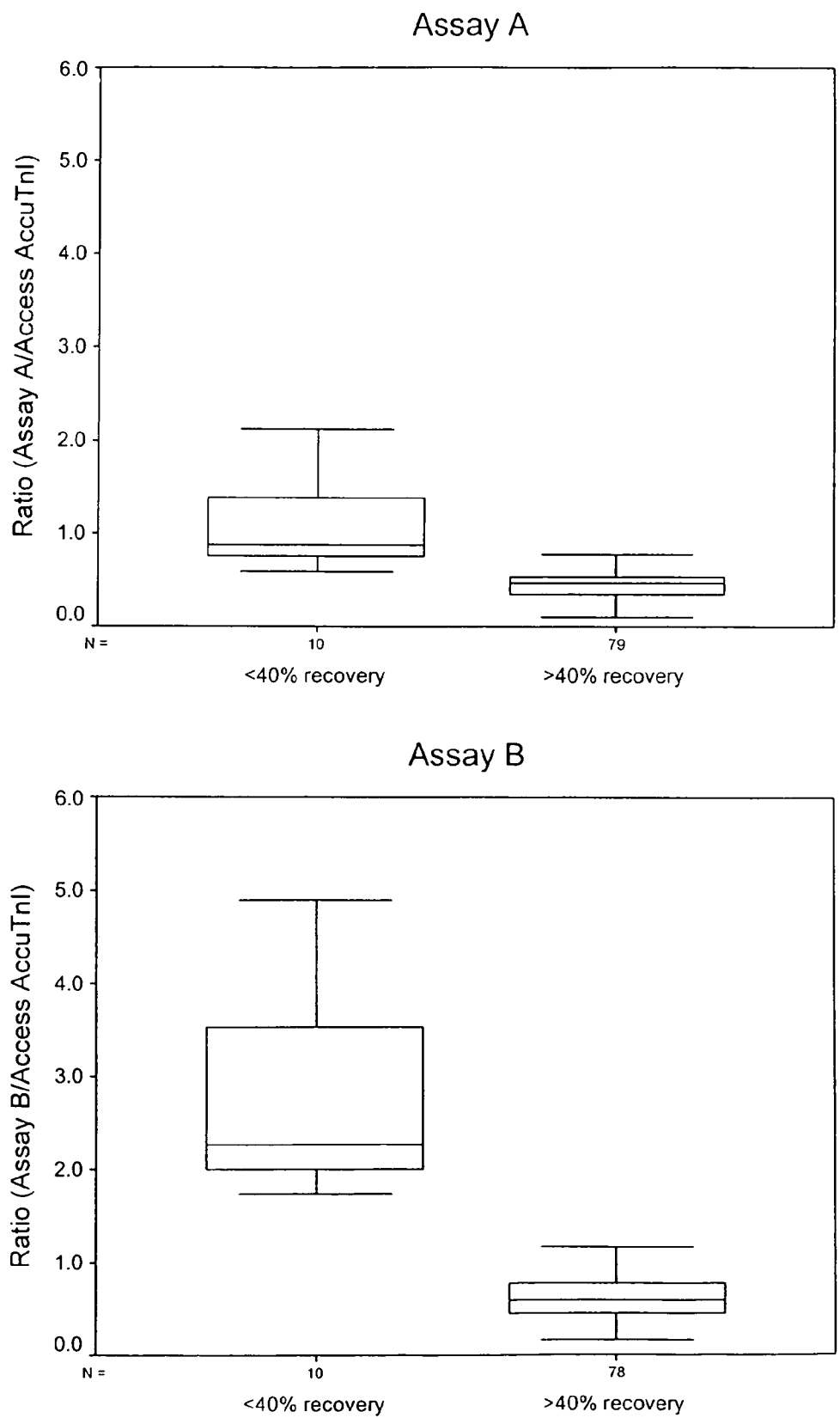
FIG. 7 shows the relative concentration cTnI for assays according to this invention, Assay A and B, compared to a commercial assay, for recovery below 40% and for recovery above 40%.

The analytical recovery of added cTnI (3 µg/L) was measured with the Mab 1/Mab 2 assay (which is affected by the presence of IF) in samples taken at admission from 52 patients presenting with chest pain. Another sample was taken approximately 6 hours later. The box-whisker plots (FIG. 7) show the concentration ratio of the new assays to Beckman Access AccuTnI, with the samples grouped according to the recovery of cTnI in the admission sample (</>40%). The mean ratio of Assay A to Access AccuTnI was 1.038 in samples with recovery <40% and 0.462 in samples with recovery >40%. The mean ratio of Assay B to Access AccuTnI was 2.858 in samples with recovery <40% and 0.614 in samples with recovery >40%. The difference between the mean in samples with recoveries <40% or >40% was statistically different in an independent samples t-test (p=0.004 for Assay A, p<0.001 for Assay B). The median recovery of cTnI was 65.0% in the 52 admission samples. Results that were below the detection limit of Assays A and B (0.012 µg/L) were not included (Assay A n=15; Assay B n=16), all of them were admission samples and had a recovery >40%.

The whiskers show the minimum and maximum values (excluding outliers), the boxes indicate the 25-75$^{th}$ percentiles and the horizontal lines indicate the median. N=indicates the number of samples in each group.

The figures show that the new assays are more sensitive than the Access AccuTnI assay for samples that have a low analytical recovery of cTnI when measured with the Mab 1/Mab 2 assay, i.e. a relatively high concentration of IF.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

1. The Joint European Society of Cardiology/American College of Cardiology Committee. Myocardial infarction redefined—a consensus document of the Joint European Society of Cardiology/American College of Cardiology Committee for the redefinition of myocardial infarction. J Am Coll Cardiol 2000; 36:959-69.
2. Wu A H, Apple F S, Gibler W B, Jesse R L, Warshaw M M, Valdes R, Jr. National Academy of Clinical Biochemistry Standards of Laboratory Practice: recommendations for the use of cardiac markers in coronary artery diseases. Clin Chem 1999; 45:1104-21.
3. Apple F S. Clinical and analytical standardization issues confronting cardiac troponin I [Opinion]. Clin Chem 1999; 45:18-20.
4. Newman D J, Olabiran Y, Bedzyk W D, Chance S, Gorman E G, Price C P. Impact of antibody specificity and calibration material on the measure of agreement between methods for cardiac troponin I. Clin Chem 1999; 45:822-8.
5. Tate J R, Heathcote D, Rayfield J, Hickman P E. The lack of standardization of cardiac troponin I assay systems. Clin Chim Acta 1999; 284:141-9.
6. Wu A H B, Feng Y-J, Moore R, Apple F S, McPherson P H, Buechler K F, et al. Characterization of cardiac troponin subunit release into serum after acute myocardial infarction and comparison of assays for troponin T and I. Clin Chem 1998; 44:1198-208.
7. Ingraham R H, Swenson C A. Binary interactions of troponin subunits. J Biol Chem 1984; 259:9544-8.
8. Katrukha A G, Bereznikova A V, Esakova T V, Pettersson K, Lovgren T, Severina M E, et al. Troponin I is released in bloodstream of patients with acute myocardial infarction not in free form but as complex. Clin Chem 1997; 43:1379-85.
9. Giuliani I, Bertinchant J P, Granier C, Laprade M, Chocron S, Toubin G, et al. Determination of cardiac troponin I forms in the blood of patients with acute myocardial infarction and patients receiving crystalloid or cold blood cardioplegia. Clin Chem 1999; 45:213-22.
10. Katrukha A, Bereznikova A, Filatov V, Esakova T. Biochemical factors influencing measurement of cardiac troponin I in serum [Review]. Clin Chem Lab Med 1999; 37:1091-5.
11. Katrukha A G, Bereznikova A V, Filatov V L, Esakova T V, Kolosova O V, Pettersson K, et al. Degradation of cardiac troponin I: implication for reliable immunodetection. Clin Chem 1998; 44:2433-40.
12. Panteghini M, Gerhardt W, Apple F S, Dati F, Ravkilde J, Wu A H. Quality specifications for cardiac troponin assays. Clin Chem Lab Med 2001; 39:175-9.
13. Bereznikova A, Katrukha A, Filatov V, Pettersson K, Esakova T, Bulargina T, et al. Monoclonal antibodies affected by cardiac troponin I phosphorylation: is part of troponin in the blood of myocardial infarction patients phosphorylated? [Abstract]. Clin Chem Lab Med 1999; 37:S448.
14. Labugger R, Organ L, Collier C, Atar D, Van Eyk J E. Extensive troponin I and T modification detected in serum from patients with acute myocardial infarction. Circulation 2000; 102:1221-6.
15. Ingraham R H, Hodges R S. Effects of Ca2+ and subunit interactions on surface accessibility of cysteine residues in cardiac troponin. Biochemistry 1988; 27:5891-8.
16. Gerhardt W, Nordin G, Herbert A-K, Linaker Burzell B, Isaksson A, Gustavsson E, et al. Troponin T and I Assays Show Decreased Concentrations in Heparin Plasma Compared with Serum: Lower Recoveries in Early than in Late Phases of Myocardial Injury. Clin Chem 2000; 46:817-21.
17. Segura R, Varela E, Marti R, Vidal E, Gonzalez C, Figueras J, et al. Comparison of three assays for cardiac 17. troponin I measurement: effect of chelating agents [Abstract]. Clin Chem Lab Med 1999; 37:457.
18. Selby C. Interference in immunoassay [Review]. Ann Clin Biochem 1999; 36:704-21.
19. Weber T H, Kapyaho K I, Tanner P. Endogenous interference in immunoassays in clinical chemistry. A review [Review]. Scand J Clin Lab Invest Suppl 1990; 201:77-82.
20. Kricka L J. Human anti-animal antibody interferences in immunological assays [Review]. Clin Chem 1999; 45:942-56.
21. Thompson R J, Jackson A P, Langlois N. Circulating antibodies to mouse monoclonal immunoglobulins in normal subjects—incidence, species specificity, and effects on a two-site assay for creatine kinase-MB isoenzyme. Clin Chem 1986; 32:476-81.
22. Vaidya H C, Beatty B G. Eliminating interference from heterophilic antibodies in a two-site immunoassay for creatine kinase MB by using F(ab')2 conjugate and polyclonal mouse IgG. Clin Chem 1992; 38:1737-42.
23. Fitzmaurice T F, Brown C, Rifai N, Wu A H, Yeo K T. False increase of cardiac troponin I with heterophilic antibodies [Technical Brief]. Clin Chem 1998; 44:2212-4.
24. Dasgupta A, Banerjee S K, Datta P. False-positive troponin I in the MEIA due to the presence of rheumatoid factors in serum. Elimination of this interference by using a polyclonal antisera against rheumatoid factors. Am J Clin Pathol 1999; 112:753-6.
25. Krahn J, Parry D M, Leroux M, Dalton J. High percentage of false positive cardiac troponin I results in patients with rheumatoid factor. Clin Biochem 1999; 32:477-80.
26. Plebani M, Mion M, Altinier S, Girotto M A, Baldo G, Zaninotto M. False-positive troponin I attributed to a macrocomplex [Letter]. Clin Chem 2002; 48:677-9.
27. Nosanchuk J S, Combs B, Abbott G. False increases of troponin I attributable to incomplete separation of serum [Letter]. Clin Chem 1999; 45:714.
28. Lagneau F, Beyne P, Letteron P, Laperche T, Marty J. Fluid therapy directly interferes with immunoassay for cardiac troponin I. Intensive Care Med 1999; 25:625-7.
29. Bohner J, von Pape K W, Hannes W, Stegmann T. False-negative immunoassay results for cardiac troponin I probably due to circulating troponin I autoantibodies [Letter]. Clin Chem 1996; 42:2046.
30. Dasgupta A, Wells A, Biddle D A. Negative interference of bilirubin and hemoglobin in the MEIA troponin I assay but not in the MEIA CK-MB assay. J Clin Lab Anal 2001; 15:76-80.
31. Pettersson K, Katajamäki T, Irjala K, Leppänen V, Majamaa-Voltti K, Laitinen P. Time-resolved fluorometry (TRF)-based immunoassay concept for rapid and quantitative determination of biochemical myocardial infarction markers from whole blood, serum and plasma. Luminescence 2000; 15:399-407.
32. Takalo H, Mukkala V M, Mikola H, Liitti P, Hemmila I. Synthesis of europium(III) chelates suitable for labeling of bioactive molecules. Bioconjug Chem 1994; 5:278-82.
33. Collinson P O, Boa F G, Gaze D C. Measurement of cardiac troponins [Review]. Ann Clin Biochem 2001; 38:423-49.
34. Lövgren T, Meriö L, Mitrunen K, Mäkinen ML, Mäkela M, Blomberg K, Palenius T, Pettersson K. One-step all-in-one dry reagent immunoassays with fluorescent europium chelate label and time-resolved fluorometry. Clin Chem 1996; 42: 1196-201

The invention claimed is:

1. An immunoassay for detection and/or quantification of cardiac troponin I (cTnI) in a sample derived from an individual's blood, comprising
   contacting said sample with at least two capture antibodies that bind to said cTnI and at least one tracer antibody that binds to said cTnI or to TnC complexed with cTnI,
   detecting a signal from said tracer antibody,
   comparing said signal against a signal obtained from a standard having a known concentration of cardiac troponin I,
   wherein a first capture antibody is directed to the N-terminal portion of cTnI, and
   wherein a second capture antibody is directed to the C-terminal portion of cTnI.
2. The immunoassay of claim 1, wherein said tracer antibody is directed to the C-terminal part of cTnI.
3. The immunoassay of claim 2, wherein said second capture antibody is directed to the epitope region 148-209 aa, and said tracer antibody is directed to the epitope 110-148 aa.
4. The immunoassay of claim 3, wherein said second capture antibody is directed to the epitope region 190-196 aa, and said tracer antibody is directed to the epitope 137-148 aa.
5. The immunoassay of claim 1, wherein a third capture antibody is directed to the N-terminal part of cTnI, and said tracer antibody is directed to TnC.
6. The immunoassay of claim 5, wherein said second capture antibody is directed to the epitope region 148-209 aa, and said third capture antibody is directed to the epitope region 1-29 aa.
7. The immunoassay of claim 5, wherein said second capture antibody is directed to the epitope region 190-196 aa, and said third capture antibody is directed to the epitope region 23-29 aa.
8. The immunoassay of claim 1, wherein the capture antibodies are attached to a solid surface and the immunoassay is carried out as a heterogeneous assay.
9. The immunoassay of claim 1, wherein the capture antibodies are attached to a small particle or a molecule, and the method is carried out as a homogeneous assay.
10. The immunoassay of claim 9, wherein the capture antibodies are attached to a molecule, and the homogeneous immunoassay is an energy transfer assay.
11. The immunoassay of claim 9, wherein said molecule comprises a luminescent lanthanide chelate.
12. The immunoassay of claim 1, wherein the sample is serum, plasma or whole blood.
13. The immunoassay of claim 1, with the proviso that the sample is taken and analyzed within 97 hours after presentation of the individual to a health care facility.

* * * * *